US006992494B2

(12) United States Patent
Kaiser et al.

(10) Patent No.: US 6,992,494 B2
(45) Date of Patent: Jan. 31, 2006

(54) METHOD AND APPARATUS FOR MONITORING THE PURITY AND/OR QUALITY OF STEAM

(75) Inventors: Herbert J. Kaiser, Pontoon Beach, IL (US); Michael A. Centanni, Parma, OH (US)

(73) Assignee: Steris Inc., Temecula, CA (US)

(\*) Notice: Subject to any disclaimer, the term of this patent is extended or adjusted under 35 U.S.C. 154(b) by 0 days.

(21) Appl. No.: 10/872,227

(22) Filed: Jun. 18, 2004

(65) Prior Publication Data

US 2005/0001634 A1  Jan. 6, 2005

Related U.S. Application Data

(63) Continuation-in-part of application No. 10/389,036, filed on Mar. 14, 2003, now Pat. No. 6,844,742.

(51) Int. Cl.
*G01R 27/26* (2006.01)

(52) U.S. Cl. ...................................... 324/663; 324/666

(58) Field of Classification Search ........ 324/658–666; 210/96.1, 754; 436/124, 125; 204/403.1, 204/416; 205/775, 777
See application file for complete search history.

(56) References Cited

U.S. PATENT DOCUMENTS

| | | | |
|---|---|---|---|
| 3,636,444 A | 1/1972 | Strawn et al. ................. 324/61 |
| 3,778,706 A | 12/1973 | Thompson ................... 324/61 |
| 3,816,811 A | 6/1974 | Cmelik ..................... 324/61 R |
| 4,031,742 A | 6/1977 | Michael et al. .............. 73/40.7 |
| 4,158,810 A | 6/1979 | Leskovar .................... 324/127 |
| 4,219,776 A | 8/1980 | Arulanandan ............... 324/323 |
| 4,427,772 A | 1/1984 | Kodera et al. ................ 435/27 |
| 4,509,522 A | 4/1985 | Manuccia et al. .......... 128/634 |
| 4,525,265 A | 6/1985 | Abe et al. .................... 204/403 |
| 4,674,879 A | 6/1987 | Gregorig et al. ............ 356/301 |
| 4,769,593 A * | 9/1988 | Reed et al. .................. 324/668 |
| 4,849,687 A * | 7/1989 | Sims et al. .................. 324/668 |
| 4,857,152 A | 8/1989 | Armstrong et al. ......... 204/1 T |
| 5,151,660 A | 9/1992 | Powers et al. .............. 324/689 |
| 5,157,968 A | 10/1992 | Zfira ........................... 73/149 |
| 5,171,523 A | 12/1992 | Williams ..................... 422/20 |
| 5,179,926 A | 1/1993 | Ament ........................ 123/494 |
| 5,243,858 A | 9/1993 | Erskine et al. .......... 73/204.26 |
| 5,364,510 A | 11/1994 | Carpio .................... 204/153.1 |
| 5,439,569 A | 8/1995 | Carpio .................... 204/153.1 |
| 5,459,568 A | 10/1995 | Yano et al. ................. 356/336 |
| 5,470,754 A | 11/1995 | Rounbehler et al. ........ 436/106 |
| 5,600,142 A | 2/1997 | Van Den Berg et al. ..................... 250/339.13 |
| 5,847,276 A | 12/1998 | Mimken et al. ............. 73/453 |

(Continued)

OTHER PUBLICATIONS

U.S. Appl. No. 10/896,609, filed Jul. 21, 2004, Kaiser et al., entitled: Method and Apparatus for Real Time Monitoring of Metallic Cation Concentrations in a Solution.

(Continued)

*Primary Examiner*—Anjan Deb
*Assistant Examiner*—Amy He
(74) *Attorney, Agent, or Firm*—Kusner & Jaffe; Michael A. Centanni

(57) ABSTRACT

A method and apparatus for monitoring at least one of steam purity and steam quality for steam used in a decontamination process. A capacitor is exposed to the steam, wherein the steam acts as a dielectric between the plates of the capacitor. Permittivity of the dielectric is affected by the purity and/or quality of the steam, and thus a measurement of electrical properties of the capacitor is used to monitor steam purity and/or quality.

5 Claims, 3 Drawing Sheets

U.S. PATENT DOCUMENTS

| | | | |
|---|---|---|---|
| 5,882,590 A | 3/1999 | Stewart et al. | 422/28 |
| 5,997,685 A | 12/1999 | Radhamohan et al. | 156/345 |
| 6,162,409 A | 12/2000 | Skelley et al. | 423/239.1 |
| 6,369,387 B1 | 4/2002 | Eckles | 250/343 |
| 6,454,874 B1 | 9/2002 | Jacobs et al. | 134/18 |
| 6,614,242 B2 | 9/2003 | Matter et al. | 324/698 |
| 6,660,231 B2 | 12/2003 | Moseley | 422/98 |
| 6,706,648 B2 | 3/2004 | Yamazaki et al. | 438/790 |
| 2002/0014410 A1 | 2/2002 | Silveri et al. | 204/412 |
| 2002/0033186 A1 | 3/2002 | Verhaverbeke et al. | 134/26 |
| 2002/0076492 A1 | 6/2002 | Loan et al. | 427/255.28 |
| 2002/0109511 A1 | 8/2002 | Frank | 324/663 |
| 2002/0111040 A1 | 8/2002 | Yamazaki et al. | 438/783 |
| 2002/0157686 A1 | 10/2002 | Kenny et al. | 134/1.3 |
| 2003/0063997 A1 | 4/2003 | Fryer et al. | 422/3 |
| 2003/0102007 A1 | 6/2003 | Kaiser | 134/1 |
| 2003/0157587 A1 | 8/2003 | Gomez et al. | 435/30 |
| 2004/0029257 A1 | 2/2004 | Dutil et al. | 435/266 |
| 2004/0079395 A1 | 4/2004 | Kim et al. | 134/30 |
| 2004/0178799 A1 | 9/2004 | Korenev et al. | 324/453 |
| 2004/0178802 A1 | 9/2004 | Centanni | 324/662 |
| 2004/0178803 A1 | 9/2004 | Centanni | 324/662 |
| 2004/0178804 A1 | 9/2004 | Allen et al. | 324/662 |
| 2004/0262170 A1 | 12/2004 | Centanni | 205/782 |

OTHER PUBLICATIONS

U.S. Appl. No. 10/900,745, filed Jul. 28, 2004, Kaiser et al., entitled: Method and Apparatus for Monitoring the State of a Chemical Solution for Decontamination of Chemical and Biological Warfare Agents.

U.S. Appl. No. 10/931,186, filed Aug. 31, 2004, Kaiser et al., entitled: Method and Apparatus for Monitoring Detergent Concentration in a Decontamination Process.

U.S. Appl. No. 10/456,378, filed Jun. 6, 2003, Centanni, entitled: Method and Apparatus for Formulating and Controlling Chemical Concentrations in a Solution.

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/667,988, filed Sep. 22, 2003, Korenev et al., entitled: Method and Apparatus for Measuring the Concentration of Hydrogen Peroxide in a Fluid.

T. J. Buckley et al., "*Toroidal Cross Capactior for Measuring the Dielectric Constant of Gases*," Review of Scientific Instruments, vol. 71, No. 7, Jul. 2000, pp. 2914-2921.

Gross et al., "*The Dielectric Constants of Water Hydrogen Peroxide and Hydrogen Peroxide-Water Mixtures*," L. Amer. Chem. Soc., vol. 72, 1950, pp. 2075-2080.

"*Humidity Sensor Theory and Behavior*" Psychometrics and Moisture, Honeywell HVAC, Nov. 27, 2002.

Philipp, "*Charge Transfer Sensing*," 1997.

Wojslaw, "*Everything You Wanted to Know About Digitally Programmable Potentiometers*," Catalyst Semiconductor, Inc., Oct. 17, 2001, Publication No. 6009.

Kittel, "*Introduction to Solid State Physics*," Fourth Edition, John Wiley & Sons, Inc., 1971.

Philipp, "*The Charge Transfer Sensor*," Sensors Magazine, Oct. 1999.

* cited by examiner

METHOD AND APPARATUS FOR MONITORING THE PURITY AND/OR QUALITY OF STEAM

RELATED APPLICATIONS

This application is a continuation-in-part of U.S. patent application Ser. No. 10/389,036, filed Mar. 14, 2003 now U.S. Pat. No. 6,844,742, entitled "Method and Apparatus for Measuring Chemical Concentration in a Fluid," and is hereby fully incorporated herein by reference.

FIELD OF THE INVENTION

The present invention relates generally to decontamination systems, and more particularly to a method and apparatus for monitoring the quality and/or purity of steam used in a decontamination system, such as a steam sterilizer.

BACKGROUND OF THE INVENTION

As used herein, the term "decontamination" refers to processes, including, but not limited to, "deactivation of biocontamination," "deactivation of chemical contamination," "sterilization," "disinfection" and "sanitization."

Steam is commonly used in decontamination systems, such as sterilizers. In this regard, steam sterilizers are widely used in hospitals, doctors offices, dentist offices, and laboratories to sterilize medical and dental instruments, laboratory instruments, production equipment, manufactured products, and other articles.

"Steam purity" and "steam quality" are important properties of steam that will affect the efficacy of a decontamination process, such as steam sterilization. Steam purity is an expression of the quantity of non-water components (i.e., solid, liquid or vaporous contamination) carried in the steam. Steam quality refers to the quantity of moisture present in the steam. If there is no moisture (i.e., no liquid water), then the steam is of 100% quality. Accordingly, "pure" steam has a liquid water content of 0%. It should be appreciated that steam quality relates to steam purity because liquid droplets in steam may contain dissolved solids.

A steam generator used to vaporize water can introduce contaminants into the steam, thereby reducing steam purity. For example, where the steam generator is a boiler, boiler chemicals can be introduced into the steam during priming or foaming of the boiler. These contaminants may cause corrosion or staining of the decontamination device (e.g., steam sterilizer) or articles to be processed by the decontamination device.

Steam purity is typically measured by performing chemical analysis on the steam. In this regard, samples of steam are collected by means of an apparatus referred to as a steam cooler, or by collecting the steam as condensate.

In many healthcare applications, the minimum acceptable steam quality for a steam sterilizer is 95%. If steam quality is below 95%, then "wet packs" (i.e., moisture droplets) may develop on articles after completion of a sterilization cycle. Consquently, reprocessing will be required.

Steam quality is typically measured in the following ways: (1) using a plumbed-in device that physically separates condensed water from the steam, or (2) collecting steam using a steam cooler, and analyzing the steam for sodium content.

Steam purity and steam quality measurements are time consuming, often innaccurate, and can expose an operator to potentially unsafe conditions. Moreover, prior art approaches to measuring steam purity and steam quality do not provide advanced warnings of problems with the purity and quality of the steam used in a decontamination process.

The present invention provides a method and apparatus for monitoring the purity and/or quality of steam that addresses these and other problems.

SUMMARY OF THE INVENTION

In accordance with a first aspect of the present invention, there is provided a system for monitoring at least one of steam purity and steam quality, comprising: (a) a capacitor having first and second plates exposed to steam, said steam being a dielectric therebetween, wherein said capacitor has a capacitance $C_x$; and (b) processing means for determining a change in an electrical property of the capacitor, said change in the electrical property varying according to at least one of steam purity and steam quality.

In accordance with another aspect of the present invention, there is provided a method for monitoring at least one of steam purity and steam quality, comprising: (a) exposing a capacitor, having first and second plates, to steam, said steam comprising a dielectric therebetween; and (b) determining a change in an electrical property of the capacitor, said change in the electrical property varying according to at least one of steam purity and steam quality.

An advantage of the present invention is the provision of a method and apparatus for monitoring the purity and/or quality of steam that can provide constant monitoring of stream purity and/or quality during a decontamination process.

Another advantage of the present invention is the provision of a method and apparatus for monitoring the purity and/or quality of steam that can provide advanced warning of steam purity and steam quality problems, thus reducing or eliminating the need for reprocessing, or replacement of damaged articles.

Yet another advantage of the present invention is the provision of a method and apparatus for monitoring the purity and/or quality of steam that can record measurements to provide verification of appropriate processing conditions.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, wherein.

DETAILED DESCRIPTION OF PREFERRED EMBODIMENT

Figure 1:
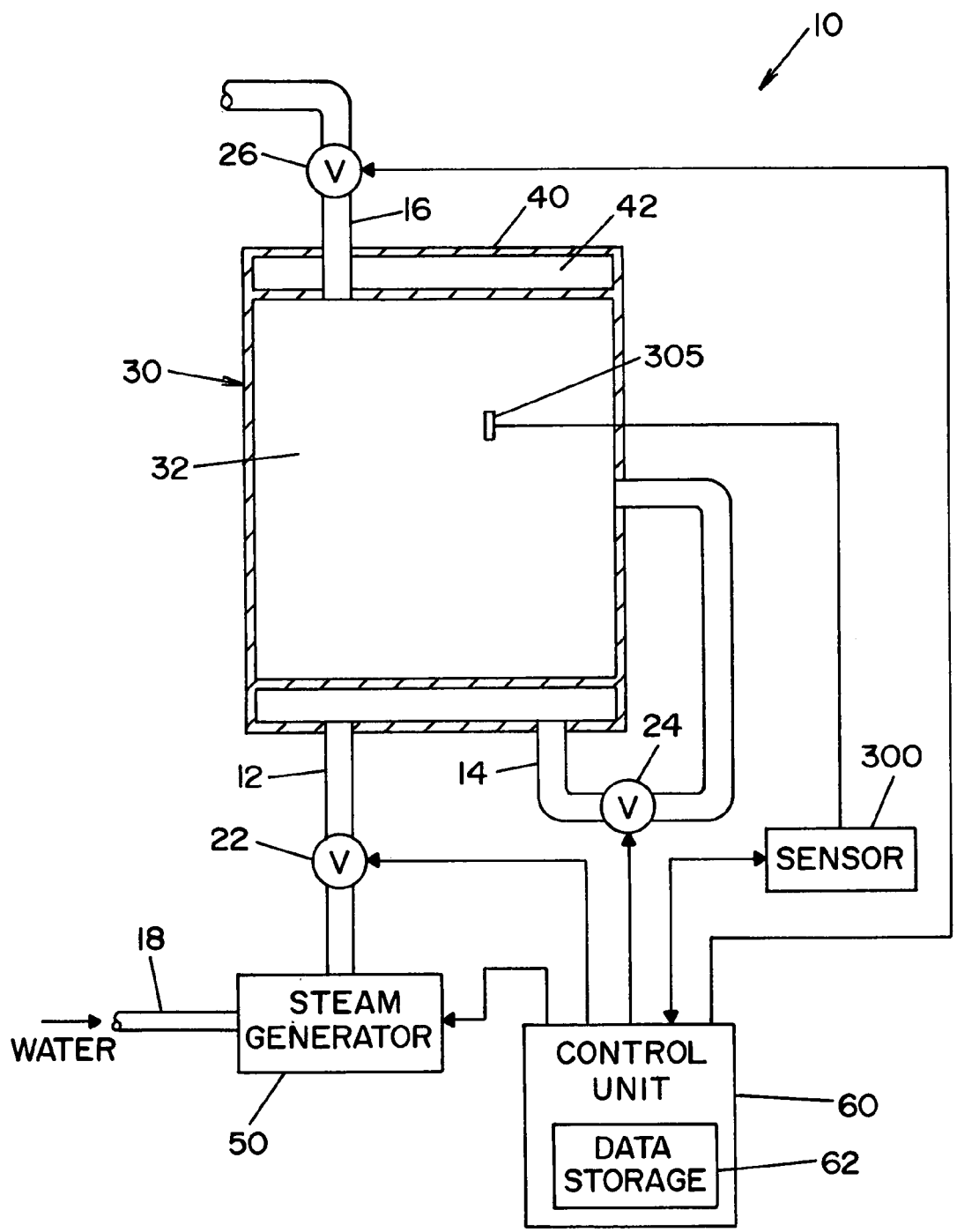
FIG. 1 is a cross-sectional side view of an exemplary steam sterilization

Referring now to the drawings wherein the showings are for the purpose of illustrating a preferred embodiment of the invention only, and not for the purpose of limiting same, FIG. 1 shows a steam sterilization system 10 having sensor 300 for monitoring the purity and/or quality of steam used within system 10. In the illustrated embodiment, system 10 is a steam sterilization system for sterilizing articles with steam. It should be understood that while a preferred embodiment of the present invention is described with reference to a steam sterilization system, it is contemplated that the present invention may be used in connection with other decontamination systems and facilities that utilize steam.

Steam sterilization system 10 is generally comprised of a vessel 30, an outer jacket 40, a steam generator 50, a control unit 60, and a sensor 300.

Vessel 30 defines a chamber 32. In the illustrated embodiment, vessel 30 is preferably cylindrical or rectangular in shape. Articles being sterilized are placed into chamber 32 for exposure to steam. Steam is released from chamber 32 through an outlet conduit 16. A valve 26 controls the release of steam from chamber 32.

Outer jacket 40 surrounds vessel 30 and defines a region 42 between vessel 30 and outer jacket 40 for injection of steam. Outer jacket 40 is also preferably cylindrical or rectangular in shape. A conduit 14 connects region 42 with chamber 32. A valve 24 controls the flow of steam between region 42 and chamber 32.

Steam generator 50 produces steam by means well known to those skilled in the art. For instance, steam generator 50 may take the form of a conventional electric boiler. Water is supplied to steam generator 50 by a water input conduit 18. Steam produced by steam generator 50 is supplied to region 42 by a first conduit 12. A valve 22 controls the flow of steam into region 42.

Control unit 60 is a preferably a microprocessor or a microcontroller programmed to control operation of system 10. In this regard, control unit 60 controls the operation of steam generator 50, and valves 22, 24 and 26. Control unit 60 also preferably includes (or is connected with) a data storage device 62 for storing data.

Figure 2:
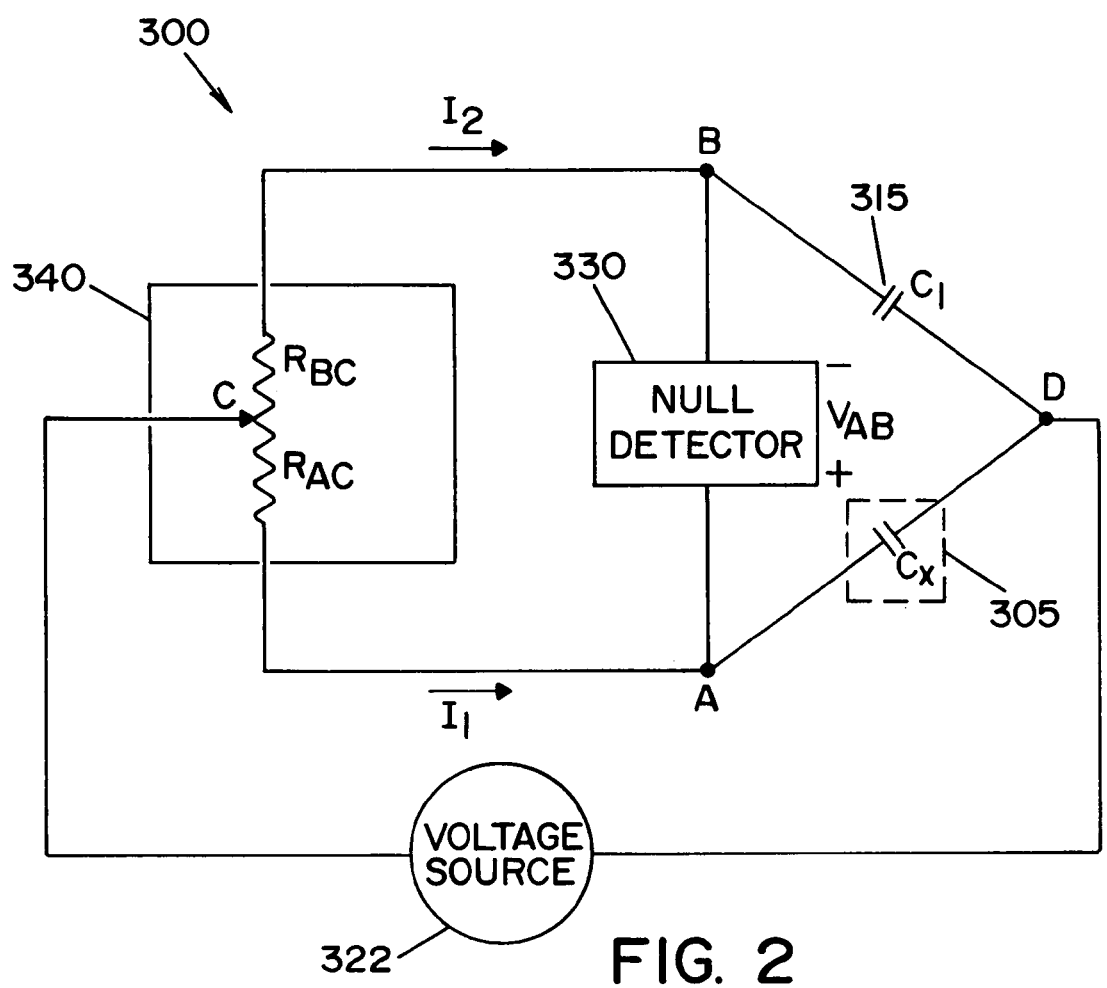
FIG. 2 is a schematic diagram of an exemplary capacitive sensor for monitoring the purity and/or quality of steam used in a steam sterilization system, according to a first embodiment.

Sensor 300 may take the form of any suitable sensing device responsive to changes in the purity and/or quality of steam used within system 10. An exemplary sensor 300, is shown in FIG. 2. Sensor 300 is described in detail in U.S. patent application Ser. No. 10/389,036, filed Mar. 14, 2003, entitled "Method and Apparatus for Measuring Chemical Concentration in a Fluid," and U.S. patent application Ser. No. 10/405,880, filed Apr. 2, 2003, entitled "Method and Apparatus for Measuring Concentration of a Chemical Component in a Gas Mixture," which are fully incorporated herein in their entirety.

Broadly stated, sensor 300 includes a capacitor 305 that acts as a sensing element. Capacitor 305 is preferably disposed within chamber 32, but it is also contemplated that capacitor 305 could be located in alternative locations where it is exposed to the steam, including, but not limited to, region 42, and conduits 12, 14 or 16. Furthermore, it is contemplated that more than one sensor 300 could be included in system 10, to allow for monitoring of steam purity and/or steam quality at multiple locations therein.

Electrical properties of capacitor 305 are responsive to steam used in system 10. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules. The dielectric constant of steam is approximately 1. The introduction of impurities (i.e., contaminants) into the steam will cause the dielectric constant of the steam to change. For example, the introduction of ionic species (e.g., sodium, potassium, etc.) or organic contaminates (e.g., amines) will result in changes to the dielectric constant. The presence of condensed water in the steam will generally cause an increase in the dielectric constant, since the dielectric constant of liquid water is approximately 80. Accordingly, sensor 300 can be used to ascertain a measure of steam purity and/or steam quality.

According to the embodiment illustrated in FIG. 2, sensor 300 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. The bridge circuit is used to determine a capacitance value indicative of the purity and/or quality of the steam used in system 10.

Sensor 300 is generally comprised of a voltage source 322, a null detector 330, an electronic potentiometer 340, a capacitor 315 of a known capacitance $C_1$, and capacitor 305 having a capacitance $C_x$.

Capacitor 305 is directly exposed to steam inside chamber 32. Steam fills the gap between the conducting plates of capacitor 305, thereby acting as the insulator or "dielectric" of capacitor 305. Since the dielectric constant of the steam will vary in accordance with steam purity and quality, capacitance $C_x$ of capacitor 305 will likewise vary in accordance with steam purity and quality.

In a preferred embodiment, capacitor 305 is a parallel plate capacitor., However, it should be appreciated that capacitor 305 could be constructed in a different form. For example, capacitor 305 could be a cylindrical or spherical capacitor. If a spherical capacitor is used as capacitor 305, holes must be placed in the outer shell of capacitor 305 such that steam can enter and exit the capacitor.

Electronic potentiometer 340 functions in the same manner as a mechanical potentiometer. In this regard, electronic potentiometer 340 is a three terminal device. Between two of the terminals is a resistive element. The third terminal known as the "wiper" is connected to various points along the resistive element. In the illustrated embodiment, the wiper is digitally controlled by control unit 60. The wiper divides the resistive element into two resistors $R_{BC}$ and $R_{AC}$. Electronic potentiometer 340 may take the form of a digitally programmable potentiometer (DPPTM) available from Catalyst Semiconductor, Inc. of Sunnyvale, Calif.

In a preferred embodiment, voltage source 322 provides an AC voltage signal, such as a sinusoidal or pulse waveform. Null detector 330 is a device for detecting a null condition (i.e., a short circuit), such as a galvanometer, a voltmeter, a frequency-selective amplifier, and the like.

Operation of sensor 300 will now be described in detail. The elements of the bridge circuit are connected between junctions AC, BC, AD, and BD. Electronic potentiometer 340 is operated by control unit 60 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC} = V_{BC}, \text{ and } V_{AD} = V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC} = V_{BD}/V_{BC}$$

$$V_{AD} = V_{BD}/(V_{AC}/V_{BC})$$

Capacitor 305 of capacitance $C_x$ is connected between junctions A and D, and capacitor 315 of known capacitance $C_1$, is connected between junctions B and D. Electronic potentiometer 340, connected from junction A to junction C to junction B is adjusted by control unit 60 to vary the voltages $V_{AC}$ and $V_{BC}$.

When a null is detected by null detector 330, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC} = I_1 R_{AC} \text{ and } V_{BC} = I_2 R_{BC}.$$

The voltage across a capacitor with capacitance C, current I, and frequency is:

$$V = \frac{I}{2\pi f C}$$

Therefore, the voltages $V_{AD}$ and $V_{BD}$ may be expressed as:

$$V_{AD} = \frac{I_1}{2\pi f C_x} \quad V_{BD} = \frac{I_2}{2\pi f C_1}$$

As discussed above, $V_{AD} = V_{BD}/(V_{AC}/V_{BC})$, $V_{AC} = I_1 R_{AC}$, and $V_{BC} = I_2 R_{BC}$. Therefore, $$C_x = C_1 \left( \frac{R_{BC}}{R_{AC}} \right).$$

In view of the forgoing relationship, when a null condition is detected, the resistance values for $R_{BC}$ and $R_{AC}$, along with the known capacitance $C_1$ of capacitor 315, can be used to determine the unknown value of capacitance $C_x$ of capacitor 305.

Differences in dipole moments of different molecules are used to monitor steam purity and/or quality. As discussed above, steam fills the gap between the conducting plates of capacitor 305, thereby acting as the dielectric of capacitor 305 By configuring capacitor 305 as an element of a bridge circuit, a measure of resistance values $R_{AC}$ and $R_{BC}$, when the bridge is balanced or nulled, can be used to determine the capacitance $C_x$ of capacitor 305. The capacitance $C_x$ of capacitor 305 is indicative of the purity and/or quality of the steam in chamber 32, since the premittivity of the respective dielectric is affected by the presence of contaminants and condensed water in the steam.

It is well known that for a parallel plate capacitor $C = (k\epsilon_0)(A/d) = (\epsilon)(A/d)$ where C is capacitance, k is the dielectric constant, $\epsilon_0$ is the permittivity of free space ($8.85 \times 10^{-12}$ F/m), is the permittivity (Farads/meter) of the capacitor dielectric, A is the area of the capacitor plates (m$^2$), and d is the separation in meters between the capacitor plates. As $\epsilon$ increases, the capacitance C will increase. Where citor is a parallel plate capacitor with circular plates of diameter D, $C = (\pi D^2 \epsilon)/(4d)$.

It will be appreciated that the dielectric constant k of the capacitor can be determined according to the following expression:

$$k = \frac{4dC}{\pi D^2 \varepsilon_0},$$

where the value of capacitance, C, is determined as discussed above. The dielectric constant of the capacitor can also be determined by determining the capacitance with the dielectric in place between the conducting plates ($C_d$), and then determine the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c = 1/(2\pi f C)$). Accordingly, frequency of the waveform generated by voltage source 322 influences the response of capacitors.

Figure 3:
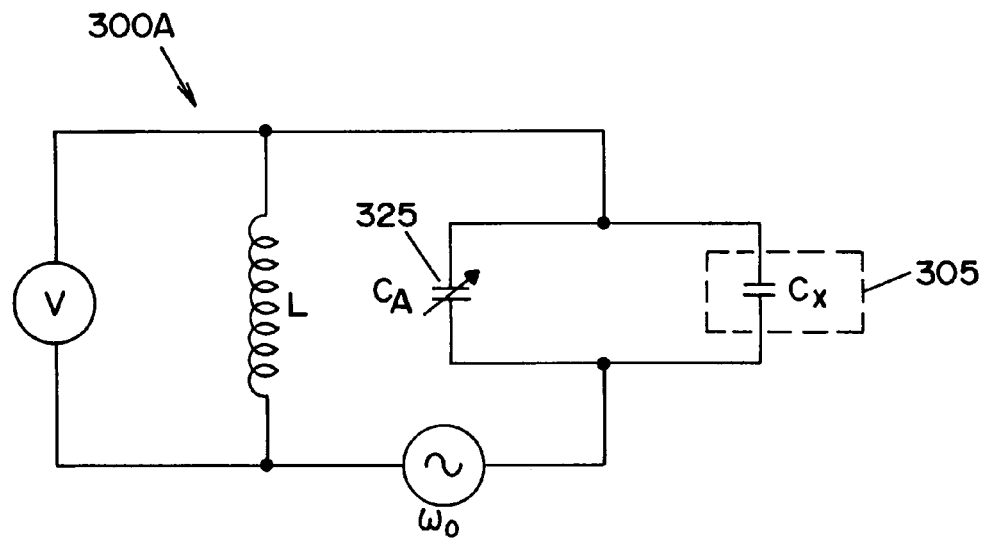
FIG. 3 is a schematic diagram of an exemplary capacitive sensor for monitoring the purity and/or quality of steam used in a steam sterilization system, according to a second embodiment.

It should be appreciated that while the embodiment illustrated in FIG. 2 includes a sensor 300 in the form of a bridge circuit, other types of circuits and techniques (including other types of bridge circuits, and capacitance meters) known to those skilled in the art, may be suitably used to measure capacitance. For example, FIG. 3 illustrates an alternative sensor 300A. Sensor 300A is an LC resonant circuit, including a variable capacitor 325 (having a capacitance $C_A$), and capacitor 305 (having a capacitance $C_x$) that acts as the sensing element, as described above. Since the resonance frequency $\omega_0 = [L(C_A + C_x)]^{-1/2}$, the unknown capacitance $C_x$ of capacitor 305 can be determined.

Figure 4:
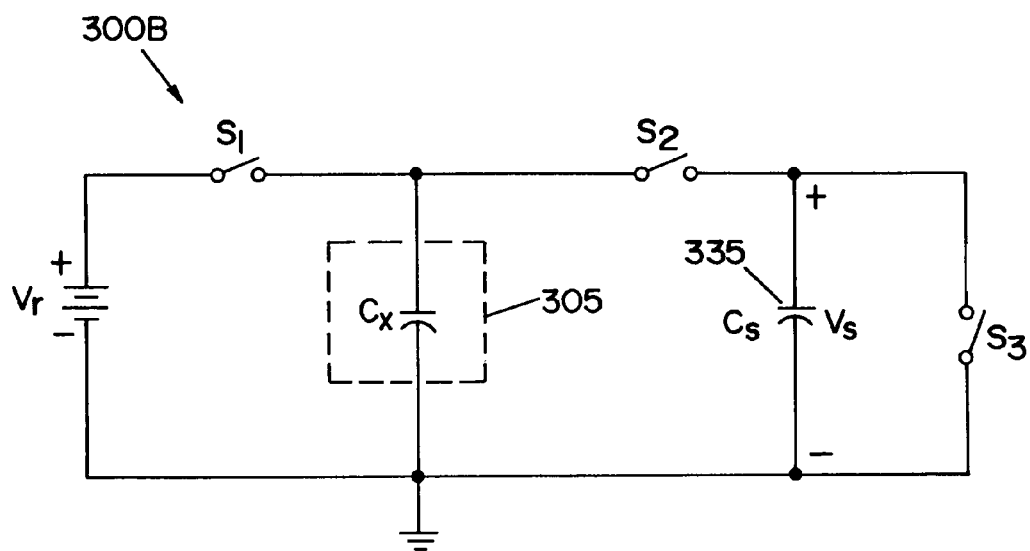
FIG. 4 is a schematic diagram of an exemplary capacitive sensor for monitoring the purity and/or quality of steam used in a steam sterilization system, according to a third embodiment.

FIG. 4 illustrates yet another alternative sensor 300B suitable for use in connection with the present invention. Sensor 300B is a "charge transfer" sensor circuit. Charge transfer sensor circuits are recognized to provide resolutions of fractions of a femtoFarad. In a charge transfer sensor circuit the unknown capacitance $C_x$ of a sense electrode is determined by charging the sense electrode to a fixed potential, and then transferring that charge to a charge detector comprising a capacitor 335 of known capacitance $C_s$. In sensor 300B, capacitor 305 of unknown capacitance $C_x$ acts as a sensing element, as described above. In this regard, steam fills the gap between the conducting plates of capacitor 305, thereby acting as an insulator or "dielectric" of capacitor 305. Capacitor 305 is first connected to a DC reference voltage ($V_r$) via a switch $S_1$. Switch $S_1$ is reopened after capacitor 305 is satisfactorily charged to the potential of $V_r$. Then, after as brief as possible a delay so as to minimize leakage effects caused by conductance, switch $S_2$ is closed and the charge (Q) present on capacitor 305 is transferred to capacitor 335 (i.e., the charge detector). Once the charge Q is satisfactorily transferred to capacitor 335, switch $S_2$ is reopened. By reading voltage $V_s$, the capacitance $C_x$ of capacitor 305 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, capacitor 335 is selected to be significantly larger than capacitor 305.

The equations governing sensor 300B are as follows:

$$V_s = V_r[C_y/(C_y+C_s)], \text{ therefore}$$

$$C_y = V_s C_s/[V_r - V_s].$$

The charge-transfer sensor has been applied in a self-contained capacitance-to-digital-converter (CDC) integrated circuit (IC). For example, Quantum Research Group produces a QProx™ CDC sensor IC (e.g., QT300 and QT301 CDC sensor ICs) for detecting femtofarad level changes in capacitance. The CDC sensor IC outputs a digital value corresponding to the detected input capacitance. The value of an external sampling capacitor controls the gain of the sensor.

Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from 10–7 pF to 10 $\mu$F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCS) can easily obtain resolutions to 0.01 pF.

Referring now to FIG. 2, monitoring of steam purity and/or steam quality using capacitor 305 of capacitance $C_x$ will now be described in connection with sensor 300.

As a preliminary step, capacitor 305 is first nulled in air, and a value is obtained for capacitance $C_x$ of capacitor 305 in the presence of steam having no contaminants and 100% steam quality. This value for capacitance $C_x$ is then preferably stored in data storage device 62 as a setpoint value. As indicated above, steam having no contaminants and no condensed water has a dielectric constant of approximately 1. Determination of values for $R_{AC}$ and $R_{BC}$ when the bridge is nulled can be used to determine a value for the capacitance $C_x$ of capacitor 305, since $C_x = C_1 (R_{BC}/R_{AC})$. Sensor 300 can now be used to monitor steam purity and/or quality in chamber 32 during a decontamination cycle, as follows.

Capacitor 305 is exposed to steam in chamber 32 during a decontamination cycle. The measured capacitance $C_x$ of capacitor 305 is compared to the capacitance $C_x$ of capacitor 305 associated with steam having no contaminants and 100% steam quality (i.e., the setpoint value). If the measured capacitance $C_x$ differs a predetermined amount from the setpoint value, then it is determined that the steam includes contaminants and/or condensed water. The predetermined amount may be selected to take into consideration acceptable ranges for steam purity and steam quality.

Furthermore, it is believed that changes in steam purity generally result in relatively small changes in the dielectric constant of the steam (and hence relatively small changes capacitance $C_x$), whereas changes in steam quality generally result in relatively large changes in the dielectric constant of the steam (and hence relatively large changes in capacitance $C_x$). Accordingly, changes in steam purity may be distinguishable from changes in steam quality by reference to the difference between the setpoint value and the measured capacitance $C_x$.

It should be appreciated that while a preferred embodiment of the present invention uses a measure of a capacitor's capacitance to monitor steam purity and/or quality, it is also contemplated that a measure of other electrical properties associated with a capacitor may be used to monitor steam purity and/or quality, including, but not limited to, the permittivity and dielectric constant of the capacitor dielectric.

The present invention shall now be further described with reference to the general operation of system 10 (see FIG. 1). System 10 is operated by placing articles in chamber 32. Chamber 32 is preheated by pumping saturated steam from steam generator 50 into region 42, via first conduit 12. After region 42 is charged with steam, saturated steam is injected into chamber 32 via second conduit 14. During a decontamination cycle sensor 300 monitors steam inside chamber 32. In the event that it is determined that the steam does not comply with the required steam purity and/or quality, then control unit 60 may provide an audible and/or visual indicator to the operator. Furthermore, it may be necessary to take corrective action, including reprocessing the articles in chamber 32. Data collected by sensor 300 during decontamination cycles may be stored in data storage device 62 to provide historical data for verification of appropriate decontamination processing conditions.

At the end of a decontamination cycle, steam is pumped out of chamber 32 via outlet conduit 16, and chamber 32 is evacuated to a pressure below atmospheric pressure to remove any moisture remaining in chamber 32 or on articles therein. Steam pumped out of chamber 32 may be condensed, and may be recycled to steam generator 80 via water inlet conduit 18.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A system for monitoring at least one of steam purity and steam quality in a chamber during a decontamination process, comprising:

a capacitor having first and second conducting elements exposed to steam, said steam being a dielectric therebetween, wherein said capacitor has a capacitance $C_x$;

a data storage device for storing a setpoint value, wherein said setpoint value is associated with an electrical property of the capacitor; and processing means responsive to changes in the electrical property of the capacitor, said change in the electrical property varying according to changes in at least one of steam purity and steam quality during the decontamination process, said processing means including:

means for determining a measured value indicative of the electrical property of the capacitor as the capacitor is exposed to the steam; and means for determining whether the measured value differs a predetermined amount from the setpoint value, wherein said processing means controls the operation of the following:

(a) a first valve for controlling the flow of steam supplied to a region in fluid communication with the chamber;
(b) a second valve for controlling the flow of steam from the region to the chamber; and
(c) a third valve for controlling the release of steam from the chamber.

2. A system according to claim 1, wherein said processing means controls operation of a steam generator that supplies steam to said chamber.

3. A system according to claim 1, wherein said system further comprises:

a bridge circuit, wherein said capacitor forms a part of the bridge circuit.

4. A system according to claim 1, wherein said system further comprises:

a charge transfer sensor circuit, wherein said capacitor forms a part of the charge transfer sensor circuit.

5. A system according to claim 1, wherein said setpoint value is indicative of steam having no contaminants and 100% quality.

* * * * *